United States Patent [19]

Cesa et al.

[11] Patent Number: 4,929,755

[45] Date of Patent: May 29, 1990

[54] PROCESS FOR MAKING AN OPTICALLY ACTIVE MIXTURE OF AN N-ACYL-AMINO ACID OR ESTER CONTAINING AT LEAST TWO CHIRAL CENTERS

[75] Inventors: Mark C. Cesa, South Euclid; Robert A. Dubbert, Solon; James D. Burrington, Richmond Heights, all of Ohio

[73] Assignee: The Standard Oil Company, Cleveland, Ohio

[21] Appl. No.: 943,480

[22] Filed: Dec. 19, 1986

Related U.S. Application Data

[63] Continuation of Ser. No. 784,977, Oct. 7, 1985, abandoned.

[51] Int. Cl.$^5$ .............................................. C07C 99/00
[52] U.S. Cl. ..................................... 562/443; 560/16; 560/40; 560/41; 560/153; 560/164; 560/170; 560/171; 548/344; 548/479; 548/533; 548/535; 562/445; 562/446; 562/493; 562/557; 562/559; 562/561; 562/563; 562/567; 562/571; 562/573; 562/575; 562/590; 562/601

[58] Field of Search ............... 562/443, 521, 406, 446, 562/445, 493, 557, 559, 561, 563, 567, 571, 573, 575, 590, 607; 560/97, 233, 33, 35, 41, 16, 40, 153, 169, 170, 171; 548/344, 497, 533, 535

[56] References Cited

U.S. PATENT DOCUMENTS

4,439,618  3/1984  Comelti et al. ..................... 562/406
4,451,407  5/1984  Pesa et al. ........................... 560/233

FOREIGN PATENT DOCUMENTS

0145265  6/1985  European Pat. Off. ............ 562/443

Primary Examiner—James H. Reamer
Attorney, Agent, or Firm—C. S. Lynch; D. J. Untener; L. W. Evans

[57] ABSTRACT

In the process of hydrocarboxylating an α-enamide with CO and $H_2O$ or an organic hydroxyl compound to produce an N-acyl-α-amino acid or ester, respectively, the improvement comprising using as the α-enamide reactant, an α-enamide which has a chiral center that is essentially all L or D, thereby producing a reaction mixture containing diastereomeric N-acyl-α-amino acids or esters having two chiral centers, said mixture having essentially no enantiomeric pairs.

8 Claims, No Drawings

PROCESS FOR MAKING AN OPTICALLY ACTIVE MIXTURE OF AN N-ACYL-AMINO ACID OR ESTER CONTAINING AT LEAST TWO CHIRAL CENTERS

This is a File Wrapper Continuation of application Ser. No. 784,977 filed Oct. 7, 1985, now abandoned.

This invention relates to a process for making an optically active mixture of an N-acyl-amino acid or ester containing at least two chiral centers.

The separation of enantiomers by physical means such as fractional distillation or fractional crystallization and the like is known to be highly difficult in general.

It is an object of the invention to provide a process to produce a reaction mixture containing certain α-carboxy amides (N-acyl-amino acids or esters) having two (at least) chiral centers, which mixture contains two of four possible optical configurations and contains substantially no enantiomeric pairs.

Other objects, as well as features, aspects, and advantages, of the invention will become apparent from a study of the specification, including the examples and the claims.

We have now conceived a process for making such a mixture. Thus, in accordance with the present invention we have provided a process for making a separable reaction mixture containing diastereomeric N-acyl-α-amino acids or esters having at least two chiral centers, which process comprises hydrocarboxylating and essentially optically pure α-enamide (essentially all D or all L) to produce a reaction mixture of diastereomeric N-acyl-α-amino acids or esters having two chiral centers, which mixture contains essentially no enantiomeric pairs. The hydrocarboxylation is effected using $H_2O$ or an organic hydroxyl compound, usually an aliphatic alcohol, and carbon monoxide as the hydrocarboxylation reagents in the reaction with the α-enamide.

Further, in accordance with the present invention, there is provided a process which comprises reacting a chiral enamide that is essentially free of enantiomeric pairs according to the equation:

$$R_1R_2C=C(R_3)N(R_4)COR_5 + CO + R_6OH \rightarrow R_1R_2CHC(R_3)(COOR_6)N(R_4)COR_5$$

to produce an essentially diastereomeric mixture of two N-acyl-α-amino acid esters having at least two chiral carbons, wherein (A) the carbon bonded to $R_3$ in the product is chiral, (B) $R_3$ is not the same as $-CHR_1R_2$, $-COOR_6$, or $-N(R_4)COR_5$, (C) each of $R_1$, $R_2$, $R_3$, $R_4$, $R_5$, and $R_6$ contain no ethylenic or acetylenic unsaturation, (D) each of $R_1$, $R_2$, $R_3$, $R_4$, and $R_5$ contain zero to 15 carbon atoms and is independently selected from:
(1) H, a hydrocarbyl group, an acyl group;
(2) a hydrocarbyl group substituted with acylamino, acyl-(N-hydrocarbyl) amino, formylamino and formyl-(N-hydrocarbyl) amino, hydrocarbyloxy, hydrocarbylthio, acyloxy, acylthio, carboxyl, hydrocarbyl carboxyl, hydrocarbyl thiocarboxyl, hydrocarbyl amino, dihydrocarbyl amino, hydrocarbonyl, hydrocarbyl carbonyl, 3-indolyl, carbamoyl, hydrocarbylcarbamoyl, dihydrocarbylcarbamoyl, 5-imidazolyl, 2-guanidinoyl and halo groups, with the proviso that
(3) $R_1$ and $R_2$ can additionally be selected independently from acylamino, acyl-(N-hydrocarbyl) amino, formylamino and formyl-(N-hydrocarbyl) amino, hydrocarbyloxy, hydrocarbylthio, hydrocarbyl amino, dihydrocarbyl amino, acyloxy, acylthio, carboxyl, hydrocarbyl carboxyl, hydrocarbyl thiocarboxyl, hydrocarbonyl, hydrocarbyl carbonyl, 3-indolyl, carbamoyl, hydrocarbylcarbamoyl, dihydrocarbylcarbamoyl, 5-imidazolyl, 2-guanidinoyl and halo groups, and wherein $R_6$ can additionally be a hydrocarbyl group having one or more hydroxy substituents;
(E) $R_1$ and $R_2$, $R_1$ and $R_3$, or $R_2$ and $R_3$ can be linked to form a ring, and $R_4$ can be linked with $R_1$ or $R_2$ or $R_5$ to form a ring, (F) $R_6$ contains 0 to 15, usually 1 to 15, carbon atoms and is independently selected from H, hydrocarbyl, and one of the (2) groups above, and (G) at least one of $R_1$, $R_2$, $R_3$, $R_4$, and $R_5$ contains a chiral carbon atom.

If the chiral enamide starting material essentially free of enantiomeric pairs is the L isomer, the reaction product mixture contains the diastereomeric N-acyl-α-amino acids or esters of the configurations DL and LL, where the first designation is the configuration at the alpha carbon atom and the second is the configuration of the chiral center in $R_1$, $R_2$, $R_3$, $R_4$, or $R_5$ as the case may be. If the starting material is essentially all D optical isomer, the diastereomeric reaction product mixture contains the diastereomeric N-acyl-α-amino acids or esters of the configurations DD and LD.

In the foregoing reaction $R_6$ is usually hydrocarbyl or hydrocarbyl substituted with one or more hydroxy substituents. The most common $R_6OH$ reactant is a saturated monohydric aliphatic alcohol.

In most instances $R_4$ is H or acyl in the practice of the present invention.

The process of the invention for making the diastereomeric mixture containing two (or more) stereoisomeric N-acyl-α-amino acids or esters is of importance in providing a source for relatively easily obtaining a particular stereoisomeric configuration of a given α-amino acid separated from any other stereoisomer thereof. Thus, the mixture made according to the present invention can be resolved by one of two procedures. If the chiral group in the enamide is in $R_5$, the two diastereomers are separated physically by well known means, such as fractional crystallization, fractional absorption on solid absorbents, countercurrent solvent extraction, fractional distillation where feasible, or other physical means. Thereafter, the product fractions are separately hydrolyzed in the presence of an acid or base in the conventional manner to obtain the corresponding α-amino acids and the chiral, optically active (L or D) carboxylic acid. This method is especially useful and allows an recycle of the chiral acid in an overall process to be discussed hereafter.

When $R_1$, $R_2$, $R_3$, or $R_4$ contains the chiral C atom and $R_5$ does not, the same procedure as above can be followed. Alternatively, however, the hydrolysis can be effected first and then the DL and LL (or the DD and LD) products separated by such physical means as discussed above.

The present invention is of considerable value in providing a route for making of the L form or the D form of amino acids occurring in nature. In this aspect of the invention the product is a diastereometic mixture containing N-acyl-α-amino acids or esters that are hydrolyzable to naturally occurring amino acids. The present invention is of considerable advantage when compared to present methods. Thus, optically pure amino acids are produced industrially by the following methods:

(1) fermentation
(2) hydrolysis of plant, animal or single cell protein
(3) chemical synthesis followed by enantiomeric resolution of a subsequently prepared derivative
   (a) enzymatic enantioselective hydrolysis
   (b) chemical or physical separation of diastereomers.

Each of these methods has distinct disadvantages which made them costly to operate. Fermentation methods are often quite slow, require rigidly controlled conditions and highly dilute aqueous reaction media, and usually produce a mixture of products from which isolation and purification of the desired chiral amino acid is laborious and expensive. Hydrolysis of naturally occurring protein is saddled with laborious separation problems and is limited by the intrinsic concentration of the desired amino acid(s) in the protein. Chemical amino acid syntheses produce racemic mixtures of products, in addition to their use of expensive chemical feedstocks such as expensive and toxic HCN.

In these syntheses the enantiomeric resolution is accomplished by derivatization of the amino acid racemic mixture, followed by enantioselective hydrolysis with an enzyme catalyst, and separation of the L-amino acid from the D-amino acid derivative, and racemization and recycle of the D-derivative (or optionally chemical hydrolysis of the D derivative when the D-amino acid is desired); or followed by physical separation when the derivatization is performed with a chiral reagent. These procedures add steps to the overall processes and are expensive and time and labor consuming.

Among the advantages of the present invention are:
(1) Lower cost starting materials;
(2) Initial formation of diastereiomeric products as a result of the amino acid forming reaction, not a subsequent step;
(3) Fewer process steps.

In a particularly advantageous aspect of the present invention there is provided a process which comprises (1) reacting a carboxylic acid, acid halide or anhydride, each of which is optically active and essentially all L or all D, with ammonia or a primary amine to make the corresponding amide of such acid, (2) then condensing such amide with an aldehyde to yield an optically active α-enamide which is essentially free of enantiomeric pairs, (3) effecting the process set forth hereinbefore to make the essentially diastereomeric mixture of two N-acyl-α-amino acids or esters having at least two chiral carbons, (4) separating the diastereomers by conventional physical means, (5) hydrolyzing each diastereomer to make the L and D α-amino acids, respectively, plus said carboxylic acid, and recycling at least a part of said carboxylic acid (as the acid or after conversion to the halide or anhydride) to step (1).

U.S. Pat. No. 4,710,574, issued Dec. 1, 1987 discloses the details of how to hydrocarboxylate alpha enamides with carbon monoxide and water or an organic hydroxyl compound. Reference is made to this document for the details of carrying out the hydrocarboxylation, and the disclosures of this patent in this regard are incorporated herein by reference.

It should be noted that in such a hydrocarboxylation, the alpha carbon atom in the hydrocarboxylation product is chiral. Therefore, the n-acyl-α-amino acid or ester produced is a racemic mixture of the L and D forms. If one wants either the L form or the D form without its enantiomer, the separation is difficult and expensive.

The crux of the broadest aspect of the present invention is the concept of employing an alpha enamide starting material in the foregoing reaction that is essentially all L or all D so that when the reaction is carried out, the product will contain essentially no enantiomeric pairs, as previously discussed. Since the product mixture has no enantiomeric pairs, the stereoisomers can be more easily separated by physical means that can a reaction mixture containing enantiomeric pairs.

The diastereomeric N-acyl-α-amino acid or ester mixtures of the invention are all useful, as noted, to make optically active α-amino acids by hydrolysis. The amino acids are all useful to make peptides by known methods, and these can be converted to proteins to make animal feed supplements, for instance. The amino acids can also be converted to useful solid polyamides by conventional condensation techniques, useful for thermoplastic molding of solid shapes, such as structural parts, plates, tumblers, etc.

The hydrocarboxylation reaction is carried out catalytically and can be effected continuously or in a batch operation in the liquid phase at the reaction temperatures noted hereafter. Usually it is effected in a batch operation in a solvent under pressure.

The reactant concentrations can vary widely and are not critical. For convenience, the ratio of the hydrocarboxylation reactant $R_6OH$ to the enamide should be no greater than 10/1 on a molar basis and is preferably at least 1/1. The amount of carbon monoxide can vary widely, but it is usual to carry out the reaction under a carbon monoxide pressure of zero to 3500 psig, more usually 250 to 2500 psig. The amount of catalyst can also vary widely. Most conveniently, the amount of catalyst is between 0.001 and 100 mole percent based on the enamide, more usually 0.1 to 10 mole percent.

Usually, the reaction is carried out with a solvent. The solvent should be inert under the reaction conditions and preferably dissolve the active catalyst species as well as the reactants but not necessarily all of the CO. Suitable solvents found to date include tetrahydrofuran, benzene, $CH_3CN$ and $CH_2Cl_2$, $CHCl_3$, $CH_3Cl$, hexane, $CCl_4$, toluene, ethyl ether and dimethylformamide. The now preferred solvent is tetrahydrofuran, particularly when using $(\phi_3P)_2PdCl_2$ catalyst, or other palladium compounds. Usually, the amount of solvent in the system will be such that the enamide concentration is at least about 0.01 weight percent in the solution, but not over 70 weight percent.

The reaction is normally carried out at a temperature of 0° to 250° C., preferably 20° to 150° C. However, the reaction temperature can be below or above this if desired. Reaction times on the order of 0.1 to 250 hours can be employed, with reaction times on the order of 2 to 100 hours being more convenient.

Catalysts useful in the hydrocarboxylation reaction are generally transition metal catalyst compounds, particularly coordination complexes of such metals. Palladium coordination complexes are effective, especially those complexed with phosphine such as $P\phi_3$. Cobalt coordination complexes are also effective, such as $Co_2(CO)_8$ and its phosphine- or phosphite-substituted derivatives. When CO complexes are used it is advantageous to incorporate hydrogen and a tertiary amine, pyridine or a pyridine derivative into the reaction mixture to enhance catalytic activity.

Once the hydrocarboxylation reaction is completed, the product N-acyl-α-amino acid or ester diastereomers can be recovered from the reaction system in a conventional manner, such as for example, by vacuum distillation or crystallization.

As noted, the optically active α-amino acids have numerous uses. The naturally occurring amino acids have known uses. In particular, phenylalanine can be used to make the sweetner aspartame in a known manner. See U.S. Pat. No. 3,492,131, issued Jan. 27, 1970.

The following examples are illustrative only and are not to be considered in any way limiting.

EXAMPLE 1

0.10 mol of phenylacetaldehyde and 0.20 mol of D-camphorimide are heated together with stirring to 100° C. for 30 minutes. The resultant solid, 1,1-bis(D-camphorimido)-2-phenylethane, is heated in a sublimation apparatus to 250° C. at 1 mm Hg until formation of the enamide N-styryl-D-camphorimide is complete. A 70 mL stainless steel high pressure reactor fitted with a Pyrex glass liner and magnetic stir bar is charged with THF (5 mL), $CH_3OH$ (20 μL, 0.5 mmol), $(PPh_3)_2PdCl_2$ (36 mg, 0.05 mmol), and N-styryl-D-camphorimide (0.5 mmol). The reactor is sealed, pressurized to 1000 psig with CO, and stirred for 24 hours at 100° C. The product mixture, isolated after removal of gas from the reactor vessel, is shown by gas chromatography to contain a diastereomeric mixture of N-(D-camphoryl)-D-phenylalanine methyl ester and N-(D-camphoryl)-L-phenylalanine methyl ester. The diasteromers are separated by column chromatography on silica gel with benzene-ethyl acetate eluent and are separately hydrolyzed by heating in aqueous HCl to give pure L- and D-phenylalanine, $CH_3OH$, and D-camphoric acid. The D-camphoric acid is easily recycled to D-camphorimide by treatment with $NH_3$.

EXAMPLE 2

0.10 mol of L-methoxyacetaldehyde and 0.20 mol of acetamide are heated together at 100° C. with stirring, and the product solid is heated in a sublimator at 250° C. and 1 mm Hg until formation of the enamide 1-acetamido-2-(L-menthoxy)ethene is complete. A 70 mL stainless steel high pressure reactor fitted with a Pyrex glass liner and magnetic stir bar is charged with THF (5 mL), $CH_3OH$ (20 μL, 0.5 mmol), $(PPh_3)_2PdCl_2$ (36 mg, 0.05 mmol), and 1-acetamido-2-(L-menthoxy)ethene (0.5 mmol). The reactor is sealed, pressurized to 1000 psig with CO, and stirred for 24 hours at 100° C. The product mixture, isolated after removal of gas from the reactor vessel, is shown by gas chromatography to contain a diastereomeric mixture of D-2-N-acetyl-3-(L-menthoxy)propanoic acid methyl ester and L-2-N-acetyl-3-(L-menthoxy)propanoic acid methyl ester. The diastereomer mixture is hydrolyzed by heating gently in 0.2M HCl to give a mixture of LL- and LD-menthoxyalanine and $CH_3OH$. The diastereomers are then separated by fractional crystallization, and the diastereomers are treated separately with concentrated aqueous HBr to give L- and D-serine, respectively.

EXAMPLE 3

0.10 mol of acetaldehyde and 0.20 mol of L-menthoxyacetamide are heated together at 100° C. with stirring, and the product solid is heated in a sublimator at 250° C. and 1 mm Hg until formation of the enamide L-(menthoxyacetylamino)ethene is complete. A 70 mL stainless steel high pressure reactor fitted with a Pyrex glass liner and magnetic stir bar is charged with THF (5 mL), methanol (20 μL, 0.5 mmol), $Co_2(CO)_8$ (0.05 mmol), pyridine (0.25 mmol,) and L-(menthoxyacetylamino)ethene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-alanine methyl ester and N-(L-menthoxyacetyl)-L-alanine methyl ester. Separation of these products is effected by silica gel chromatography with ether-toluene eluent, and the diastereomers are treated separately with 2N HCl solution at 100° C. for 3 hours to give pure L-alanine and D-alanine.

EXAMPLE 4

0.10 mol of 3-(ethoxycarbonyl)acetaldehyde and 0.20 mol of L-menthoxyacetamide are heated together at 100° C. with stirring, and the product solid is heated in a sublimator at 250° C. and 1 mm Hg until formation of the enamide ethyl 2-(L-menthoxyacetylamino)acrylate is complete. A 70 mL stainless steel high pressure reactor fitted with a Pyrex glass liner and magnetic stir bar is charged with THF (5 mL), ethanol (0.5 mmol), $(PPh_3)_2PdCl_2$ (36 mg, 0.05 mmol), and ethyl 2-(L-menthoxyacetylamino)acrylate (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-aspartic acid diethyl ester and N-(L-menthoxyacetyl)-L-aspartic acid diethyl ester. Separation of these products is effected by silica gel chromatography with ether-toluene eluent, and the diastereomers are treated separately with 2N HCl solution at 100° C. for 3 hours to give pure L-aspartic acid and D-aspartic acid.

EXAMPLE 5

0.10 mol of 2-(benzylthio)acetaldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-2-benzylthioethene is complete. A 70 mL stainless steel high pressure reactor fitted with a Pyrex glass liner and magnetic stir bar is charged with THF (5 mL), methanol (0.5 mmol), $(PPh_3)_2PdCl_2$ (36 mg, 0.05 mmol), and 1-(L-menthoxyacetylamino)-2-benzylthioethene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-benzylcysteine methyl ester and N-(L-menthoxyacetyl)-L-benzylcysteine methyl ester. Separation of these products is effected by silica gel chromatography with ether-toluene eluent, and the diastereomers are treated separately with 2N HCl solution at 100° C. for 3 hours to give pure L-cysteine and D-cysteine.

EXAMPLE 6

0.10 mol of 3-ethoxycarbonylpropionaldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-3-ethoxycarbonylpropene is complete. A 70 mL stainless steel high pressure reactor fitted with a Pyrex glass liner and magnetic stir bar is charged with THF (5 mL), ethanol (0.5 mmol), $(PPh_3)_2PdCl_2$ (36 mg, 0.05 mmol), and 1-(L-menthoxyacetylamino)-3-ethoxycarbonylpropene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-glutamic acid diethyl ester and N-(L-menthoxyacetyl)-L-glutamic acid diethyl ester. Separation of these products is effected by silica gel chromatography with ether-toluene eluent, and the diastereomers are treated separately with 2N HCl solution at 100° C. for 3 hours to give pure L-glutamic acid and D-glutamic acid.

EXAMPLE 7

0.10 mol of 4-oxobutyraldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-3-carbamoylpropene is complete. A 70 mL stainless steel high pressure reactor fitted with a Pyrex glass liner and magnetic stir bar is charged with THF (5 mL), methanol (0.5 mmol), $(PPh_3)_2PdCl_2$ (36 mg, 0.05 mmol), and 1-(L-menthoxyacetylamino)-3-carbamoylpropene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-glutamine methyl ester and N-(L-menthoxyacetyl)-L-glutamine methyl ester. Separation of these products is effected by silica gel chromatography with ether-toluene eluent, and the diastereomers are treated separately with 2N HCl solution at 100° C. for 3 hours to give pure L-glutamine and D-glutamine.

EXAMPLE 8

0.10 mol of imidazole-4-acetaldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-2-(4-imidazolyl)ethene is complete. A 70 mL stainless steel high pressure reactor fitted with a Pyrex glass liner and magnetic stir bar is charged with THF (5 mL), methanol (0.5 mmol), $(PPh_3)_2PdCl_2$ (36 mg, 0.05 mmol), and 1-(L-menthoxyacetylamino)-2-(4-imidazolyl)ethene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-histidine methyl ester and N-(L-menthoxyacetyl)-L-histidine methyl ester. Separation of these products is effected by silica gel chromatography with ether-toluene eluent, and the diastereomers are treated separately with 2N HCl solution at 100° C. for 3 hours to give pure L-histidine and D-histidine.

EXAMPLE 9

0.10 mol of 3-(methylthio)propanal and 0.20 mol of D-camphorimide are heated together at 100° C. with stirring, and the product solid is heated in a sublimator at 250° C. and 1 mm Hg until formation of the enamide 1-(D-camphorimido)-3-methylthiopropene is complete. A 70 mL stainless steel high pressure reactor fitted with a Pyrex glass liner and magnetic stir bar is charged with THF (5 mL), methanol (0.5 mmol), $(PPh_3)_2PdCl_2$ (36 mg, 0.05 mmol), and 1-(D-camphorimido)-3-methylthiopropene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of D-camphoryl-D-methionine methyl ester and D-camphoryl-D-methionine methyl ester. Separation of these products is effected by silica gel chromatography with ether-toluene eluent, and the diastereomers are treated separately with 2N HCl solution at 100° C. for 3 hours to give pure L-methionine and D-methionine.

EXAMPLE 10

0.10 mol of acetyloxyacetaldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-2-acetyloxyethene is complete. A 70 mL stainless steel high pressure reactor fitted with a Pyrex glass liner and magnetic stir bar is charged with THF (5 mL), methanol (0.5 mmol), $(PPh_3)_2PdCl_2$ (36 mg, 0.05 mmol), and 1-(L-menthoxyacetylamino)-2-acetyloxyethene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-serine methyl ester and N-(L-menthoxyacetyl)-L-serine methyl ester. Separation of these products is effected by silica gel chromatography with ether-toluene eluent, and the diastereomers are treated separately with 2N HCl solution at 100° C. for 3 hours to give pure L-serine and D-serine.

EXAMPLE 11

0.10 mol of indole-3-acetaldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-2-(3-indolyl)ethene is complete. A 70 mL stainless steel high pressure reactor fitted with a Pyrex glass liner and magnetic stir bar is charged with THF (5 mL), methanol (0.5 mmol), $(PPh_3)_2PdCl_2$ (36 mg, 0.05 mmol), and 1-(L-menthoxyacetylamino)-2-(3-indolyl)ethene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-tryptophan methyl ester and N-(L-menthoxyacetyl)-L-tryptophan methyl ester. Separation of these products is effected by silica gel chromatography with ether-toluene eluent, and the diastereomers are treated separately with 2N HCl solution at 100° C. for 3 hours to give pure L-tryptophan and D-tryptophan.

EXAMPLE 12

0.10 mol of p-methoxyphenylacetaldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-2-(4-methoxyphenyl)ethene is complete. A 70 mL stainless steel high pressure reactor fitted with a Pyrex glass liner and magnetic stir bar is charged with THF (5 mL), methanol (0.5 mmol), $(PPh_3)_2PdCl_2$ (36 mg, 0.05 mmol), and 1-(L-menthoxy-acetylamino)-2-(4-methoxyphenyl)ethene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-O-methyltyrosine methyl ester and N-(L-menthoxyacetyl)-L-O-methyl-tyrosine methyl ester. Separation of these products is effected by silica gel chromatography with ether-toluene eluent, and the diastereomers are treated separately with 2N HCl solution at 100° C. for 3 hours to give pure L-tyrosine and D-tyrosine.

EXAMPLE 13

0.10 mol of 3,4-diacetyloxyphenylacetaldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-2-(3,4-diacetyloxyphenyl)ethene is complete. A 70 mL stainless steel high pressure reactor fitted with a Pyrex glass liner and magnetic stir bar is charged with THF (5 mL), methanol (0.5 mmol), (PPh$_3$)$_2$PdCl$_2$ (36 mg, 0.05 mmol), and 1-(L-menthoxyacetylamino)-2-(3,4-diacetyloxyphenyl)ethene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-O,O-diacetyloxydopa methyl ester and N-(L-menthoxyacetyl)-L-O,O-diacetyloxydopa methyl ester. Separation of these products is effected by silica gel chromatography with ether-toluene eluent, and the diastereomers are treated separately with 2N HCl solution at 100° C. for 3 hours to give pure L-dopa and D-dopa.

EXAMPLE 14

0.10 mol of isobutyraldehyde and 0.20 mol of L-menthoxyacetamide are heated together at 100° C. with stirring, and the product solid is heated in a sublimator at 250° C. and 1 mm Hg until formation of the enamide 1-(L-menthoxyacetylamino)-2-methylpropene is complete. A 70 mL stainless steel high pressure reactor fitted with a Pyrex glass liner and magnetic stir bar is charged with THF (5 mL), methanol (0.5 mmol), Co$_2$(CO)$_8$ (0.05 mmol), pyridine (0.25 mmol), and 1-(L-menthoxyacetylamino)-2-methylpropene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-valine methyl ester and N-(L-menthoxyacetyl)-L-valine methyl ester. Separation of these products is effected by silica gel chromatography with ether-toluene eluent, and the diastereomers are treated separately with 2N HCl solution at 100° C. for 3 hours to give pure L-valine and D-valine.

EXAMPLE 15

0.10 mol of isovaleraldehyde and 0.20 mol of D-camphorimide are heated together at 100° C. with stirring, and the product solid is heated in a sublimator at 250° C. and 1 mm Hg until formation of the enamide 1-(D-camphorimido)-3-methyl-1-butene is complete. A 70 mL stainless steel high pressure reactor fitted with a Pyrex glass liner and magnetic stir bar is charged with THF (5 mL), methanol (0.5 mmol), Co$_2$(CO)$_8$ (0.05 mmol), pyridine (0.25 mmol), and 1-(D-camphorimido)-3-methyl-1-butene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of D-camphoryl-D-leucine methyl ester and D-camphoryl-L-leucine methyl ester. Separation of these products is effected by silica gel chromatography with ether-toluene eluent, and the diastereomers are treated separately with 2N HCl solution at 100° C. for 3 hours to give pure L-leucine and D-leucine.

EXAMPLE 16

0.10 mol of 4-acetamido-1-butyraldehyde and 0.20 mol of D-camphorimide are heated together at 100° C. with stirring, and the product solid is heated in a sublimator at 250° C. and 1 mm Hg until formation of the enamide 1-(D-camphorimido)-4-acetamido-1-butene is complete. A 70 mL stainless steel high pressure reactor fitted with a Pyrex glass liner and magnetic stir bar is charged with THF (5 mL), methanol (0.5 mmol), (PPh$_3$)$_2$PdCl$_2$ (36 mg, 0.05 mmol), and 1-(D-camphorimido)-4-acetamido-1-butene (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-D-camphoryl-N'-acetyl-D-ornithine methyl ester and N-D-camphoryl-N'-acetyl-L-ornithine methyl ester. Separation of these products is effected by silica gel chromatography with ether-toluene eluent, and the diastereomers are treated separately with 2N HCl solution at 100° C. for 3 hours to give pure L-ornithine and D-ornithine.

EXAMPLE 17

N-(L-menthoxyacetyl)-2-pyrroline is prepared by condensation of 0.1 mol of 2-pyrroline with 0.1 mol of L-menthoxyacetyl chloride. A 70 mL stainless steel high pressure reactor fitted with a Pyrex glass liner and magnetic stir bar is charged with THF (5 mL), methanol (0.5 mmol), Co$_2$(CO)$_8$ (0.05 mmol), pyridine (0.25 mmol), and N-(L-menthoxyacetyl)-2-pyrroline (0.5 mmol.) The reactor is sealed, pressurized to 1000 psig with CO, and the reaction mixture is stirred for 24 hours at 100° C. The product mixture, isolated after removal of gas from the reactor vessel, contains a mixture of N-(L-menthoxyacetyl)-D-proline methyl ester and N-(L-menthoxyacetyl)-L-proline methyl ester. Separation of these products is effected by silica gel chromatography with ether-toluene eluent, and the diastereomers are treated separately with 2N HCl solution at 100° C. for 3 hours to give pure L-proline and D-proline.

EXAMPLE 18

0.10 mol of acetaldehyde and 0.20 mol of D-camphorimide are heated together with stirring to 100° C. for 30 minutes. The resultant solid, 1,1-bis-(D-camphorimido)ethane, is heated in a sublimation apparatus to 250° C. at 1 mm Hg until formation of the enamide N-vinyl-D-camphorimide is complete. A 70 mL stainless steel high pressure reactor fitted with a Pyrex glass liner and magnetic stir bar is charged with THF (5 mL), H$_2$O (9 μL, 0.5 mmol), (PPh$_3$)$_2$PdCl$_2$ (36 mg, 0.05 mmol), and N-vinyl-D-camphorimide (0.5 mmol). The reactor is sealed, pressurized to 1000 psig with CO, and stirred for 24 hours at 100° C. The product mixture, isolated after removal of gas from the reactor vessel, is shown by gas chromatography to contain a diastereomeric mixture of N-(D-camphoryl)-D-alanine and N-(D-camphoryl)-L-alanine. The diastereomers are separated by fractional crystallization and are separately hydrolyzed by heating in aqueous HCl to give pure L- and D-alanine and D-camphoric acid. The D-camphoric acid is easily recycled to D-camphorimide by treatment with NH$_3$.

As used herein the term "hydroxyl" in the phrase "organic hydroxyl compound" excludes the hydroxyl group of a carboxylic acid group, —COOH.

As will be evident to those skilled in the art, various modifications of this invention can be made or followed in the light of the foregoing disclosure and discussion without departing from the spirit and scope of the disclosure or from the scope of the claims.

We claim:

1. A process which comprises (1) reacting a carboxylic acid, acid halide or anhydride, each of which is optically active and essentially all L or D, with ammonia or a primary amine to make the corresponding amide of such acid, (2) then condensing such amide with an aldehyde to yield an optically active α-enamide which is essentially free of enantiomeric pairs, (3) making an N-acyl-α-amino acid or ester whose α C atom and another C atom are chiral, by hydrocarboxylating said optically active α-enamide with CO and $H_2O$ or an organic hydroxyl compound to produce an N-acyl-α-amino acid or ester, respectively, having essentially no enantiomeric pairs, and containing diastereomeric N-acyl-α-amino acids or esters having two chiral centers, (4) separating the diastereomers by conventional physical means, (5) hydrolyzing each diastereomer to make the L and D α-amino acids, respectively, plus said optically active carboxylic acid, and recycling at least a part of said carboxylic acid (as the acid or after conversion to the halide or anhydride) to step (1), said hydrocarboxylating simultaneously creating (a) said N-acyl-α-amino acid or ester, (b) the chirality of said alpha C atom in L, D form and (c) the second chiral center in said N-acyl-α-amino acid or ester in essentially all L or all D form.

2. A process which comprises (1) reacting a carboxylic acid, acid halide or anhydride, each of which is optically active and essentially all L or D, with ammonia or a primary amine to make the corresponding amide of such acid, (2) then condensing such amide with an aldehyde to yield an optically active α-enamide which is essentially free of enantiomeric pairs, (3) making an N-acyl-α-amino acid ester whose α C atom and another C atom are chiral, by hydrocarboxylating said optically active α-enamide with CO and an organic hydroxyl compound to produce an N-acyl-α-amino acid ester having essentially no enantiomeric pairs, and containing diastereomeric N-acyl-α-amino acid esters having two chiral centers, (4) separating the diastereomers by conventional physical means, (5) hydrolyzing each diastereomer to make the L and D α-amino acids, respectively, plus said optically active carboxylic acid, and recycling at least a part of said carboxylic acid (as the acid or after conversion to the halide or anhydride) to step (1), said hydrocarboxylation simultaneously creating (a) said ester and (b) the chirality of said alpha C atom in L, D form and (c) the second chiral center in said ester in essentially all L or all D form.

3. A method of making a hydrocarboxylation reaction mixture having essentially no enantiomeric pairs, and containing diastereomeric N-acyl-α-amino acids or esters having two chiral centers, which comprises (1) reacting a carboxylic acid, acid halide or anhydride, each of which is optically active and has a chiral center which is essentially all L or D, with ammonia or a primary amine to make the corresponding amide of such acid, (2) condensing such amide with an aldehyde to yield an optically active α-enamide which is essentially free of enantiomeric pairs, and (3) hydrocarboxylating said optically active α-enamide with CO and $H_2O$ or an organic hydroxyl compound to produce said reaction mixture, said hydrocarboxylating simultaneously creating (a) said N-acyl-α-amino acid or ester (b) the chirality of said alpha C atom in L, D form and (c) the second chiral center in said N-acyl-α-amino acid or ester in essentially all L or all D form.

4. A method of making a hydrocarboxylation reaction mixture having essentially no enantiomeric pairs, and containing diastereomeric N-acyl-α-amino acid esters having two chiral centers, which comprises (1) reacting a carboxylic acid, halide or anhydride, each of which is optically active and has a chiral center which is essentially all L or D, with ammonia or primary amine to make the corresponding amide of such acid, (2) condensing such amide with an aldehyde to yield an optically active α-enamide which is essentially free of enantiomeric pairs, and (3) hydrocarboxylating said optically active α-enamide with CO and an organic hydroxyl compound to produce said reaction mixture, said hydrocarboxylation simultaneously creating (a) said ester and (b) the chirality of said alpha C atom in L, D form and (c) the second chiral center in said ester in essentially all L or all D form.

5. In a process for making an α-amino acid, which comprises hydrocarboxylating an α-enamide with CO and $H_2O$ or an organic hydroxyl compound to produce an N-acyl-α-amino acid or ester, respectively, whose alpha C atom is chiral, and hydrolyzing said N-acyl-α-amino acid or ester, the improvement comprising using as the α-enamide reactant, an α-enamide which also has a chiral C atom that is essentially all L or D, thereby producing a reaction mixture having essentially no enantiomeric pairs and containing diastereomeric N-acyl-α-amino acids or esters having two chiral centers, separating the diastereomers by physical means, and thereafter hydrolyzing at least one of said diastereomers to make at least the L or the D-α-amino acid in essentially enantiomerically pure form, said hydrocarboxylating simultaneously creating (1) said N-acyl-α-amino acid or ester, (2) the chirality of said alpha C atom in L, D form and (3) the second chiral center in said N-acyl-α-amino acid or ester in essentially all L or all D form.

6. In a process for making an α-amino acid, which comprises hydrocarboxylating an α-enamide with CO and an organic hydroxyl compound to produce an N-acyl-α-amino acid ester, the improvement comprising using as the α-enamide reactant, an α-enamide which also has a chiral C atom that is essentially all L or D, thereby producing a reaction mixture having essentially no enantiomeric pairs and containing diastereomeric N-acyl-α-amino acid esters having two chiral centers, separating the diastereomers by physical means, and thereafter hydrolyzing at least one of said diastereomers to make at least the L or the D-α-amino acid in essentially enantiomerically pure form, said hydrocarboxylating simultaneously creating (1) said ester, (b) the chirality of said alpha C atom in L, D form and (c) the second chiral center in said ester in essentially all L or all D form.

7. In the process of hydrocarboxylating an α-enamide with CO and H₂O or an organic hydroxyl compound to produce a N-acyl-α-amino acid or ester whose alpha C atom is chiral, the improvement comprising using as the α-enamide, an α-enamide which also has a chiral C atom that is essentially all L or D, thereby producing a reaction mixture having essentially no enantiomeric pairs and containing diastereomeric N-acyl-α-amino acids or esters having two chiral centers, said hydrocarboxylating simultaneously creating (1) said N-acyl-α-amino acid or ester, (2) the chirality of said alpha C atom in L, D form and (3) the second chiral center in said N-acyl-α-amino acid or ester in essentially all L or all D form.

8. In the process of hydrocarboxylating an α-enamide with CO and an organic hydroxyl compound to produce an N-acyl-α-amino acid ester whose alpha C atom is chiral, the improvement comprising using as the α-enamide reactant, an α-enamide which also has a chiral C atom that is essentially all L or D, thereby producing a reaction mixture containing diastereomeric N-acyl-α-amino acid esters having two chiral centers, said mixture having essentially no enantiomeric pairs, said hydrocarboxylation simultaneously creating (1) said ester (2) the chirality of said alpha C atom in L, D form and (3) the second chiral center in said ester in essentially all L or all D form.

* * * * *